US 6,643,010 B2

United States Patent
Rahbar-Dehghan

(10) Patent No.: US 6,643,010 B2
(45) Date of Patent: Nov. 4, 2003

(54) MULTIPLE MICROCHANNELS CHIP FOR BIOMOLECULE IMAGING

(75) Inventor: Fariborz Rahbar-Dehghan, Edmonton (CA)

(73) Assignee: Royce Technologies LLC, Las Vegas, NV (US)

( * ) Notice: Subject to any disclaimer, the term of this patent is extended or adjusted under 35 U.S.C. 154(b) by 354 days.

(21) Appl. No.: 09/800,801

(22) Filed: Mar. 8, 2001

(65) Prior Publication Data

US 2002/0015149 A1 Feb. 7, 2002

Related U.S. Application Data

(63) Continuation-in-part of application No. 09/634,709, filed on Aug. 7, 2000.

(51) Int. Cl.[7] ................................................ G01N 21/01
(52) U.S. Cl. ...................... 356/244; 359/398; 422/102; 435/288.4; 435/288.7
(58) Field of Search ................................. 356/244, 246; 422/102, 942, 948; 435/288.4, 288.5, 288.7; 359/398

(56) References Cited

U.S. PATENT DOCUMENTS

| | | |
|---|---|---|
| 2,956,931 A | 10/1960 | Goldberg |
| 3,107,204 A | 10/1963 | Brown et al. |
| 4,039,247 A | 8/1977 | Lawman et al. |
| 4,088,448 A | 5/1978 | Lilja et al. |
| 4,154,795 A | 5/1979 | Thorne |
| 4,319,841 A | 3/1982 | Suovaniemi et al. |
| 4,447,546 A | 5/1984 | Hirschfeld |
| 4,480,031 A | 10/1984 | Shaw |
| 4,483,925 A | 11/1984 | Noack |
| 4,493,815 A | 1/1985 | Fernwood et al. |
| 4,599,315 A | 7/1986 | Terasaki et al. |

(List continued on next page.)

OTHER PUBLICATIONS

Biomedical Photometrics, Inc.—Open–Frame microscope/MACRO scope® Web site address: http://www.confocal.com/open–frame–microscope.htm Apr. 18, 2000.
Mark Schena, PhD. Microarray Biochip Technology, Cahpter 5, The Flow–Thru Chip: A Three Dimensional Biochip Platform; 2000.

Primary Examiner—F. L. Evans

(57) ABSTRACT

A panel chip for supporting biological samples for observation with an imaging microscope. The glass panel defines a top flat surface, a bottom bearing surface, and at least a few channels extending generally parallel to each other from top to bottom surfaces. Each of the channels defines a top access mouth for ingress of biological. The channels are arranged in subgroups made of a number of unit cells. Instead of being cylindroid, these channels may form cross sectional rectangular or arcuate channels, or cross sectionally water droplet like channels. Each channel has such an inner diameter as to accommodate flow through viscosity of a biological sample containing fluid. The porous substrate that is created by slot channel can provide the maximum binding surface area per unit cell or pixel, as compared to cylindrical pores, thus achieving higher sensitivity and better imaging. Also, this panel chip is capable of being used as direct in situ synthesizing of molecules and drugs. Other impurities in test solutions are however allowed to pass freely therethrough and be least prone to blockage.

18 Claims, 12 Drawing Sheets

U.S. PATENT DOCUMENTS

| | | |
|---|---|---|
| 4,673,651 A | 6/1987 | Rothenberg et al. |
| 4,722,598 A | 2/1988 | Ford |
| 4,761,378 A | 8/1988 | Godsey |
| 4,981,345 A | 1/1991 | Berry et al. |
| 5,002,889 A | 3/1991 | Klein |
| 5,096,676 A | 3/1992 | McPherson et al. |
| 5,110,556 A | 5/1992 | Lyman et al. |
| RE34,133 E | 11/1992 | Thorne |
| 5,200,152 A | 4/1993 | Brown |
| 5,219,528 A | 6/1993 | Clark |
| 5,290,705 A | 3/1994 | Davis |
| 5,308,584 A | 5/1994 | Vauramo |
| 5,424,213 A | 6/1995 | Mougin |
| 5,457,527 A | 10/1995 | Manns et al. |
| 5,608,517 A | 3/1997 | Munk |
| 5,700,655 A | 12/1997 | Croteau et al. |
| 5,738,825 A | 4/1998 | Rudigier et al. |
| 5,840,256 A | 11/1998 | Demers et al. |
| 5,843,767 A | 12/1998 | Beattie |
| 6,022,700 A | 2/2000 | Monks et al. |
| 6,037,168 A | 3/2000 | Brown |
| 6,074,614 A | 6/2000 | Hafeman et al. |

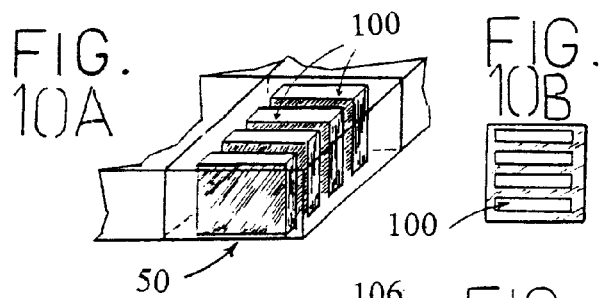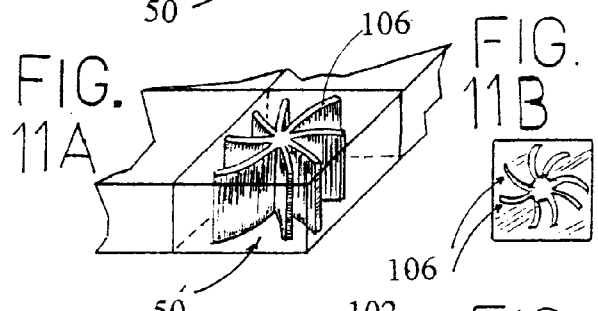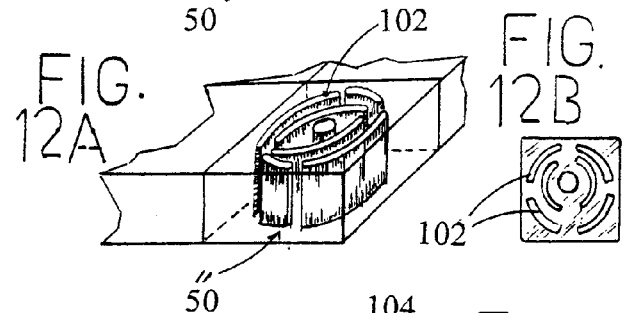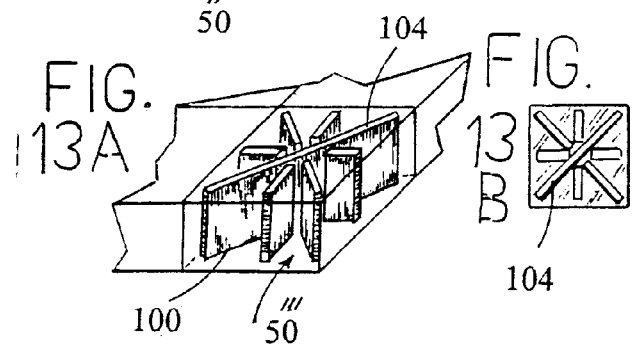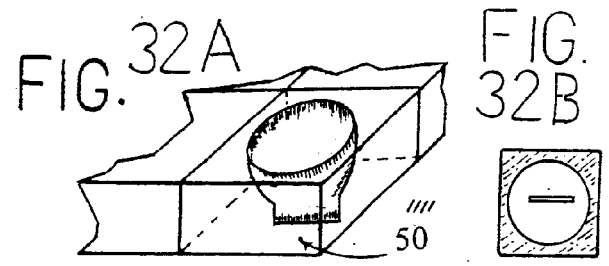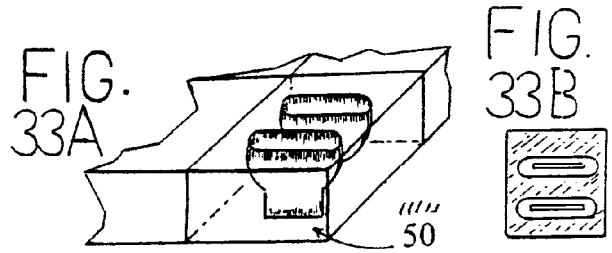

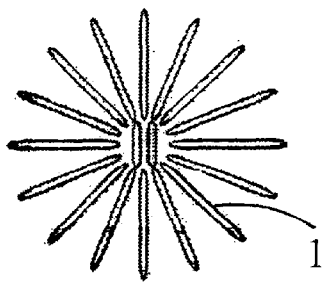 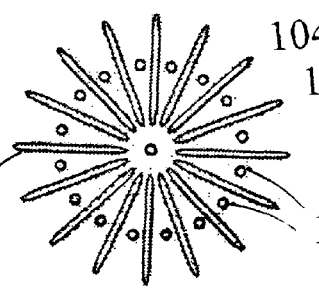 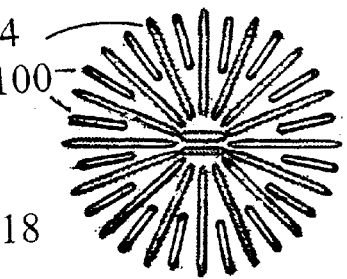
FIG. 14    FIG.15    FIG.16
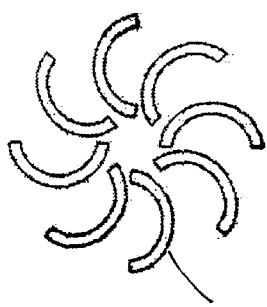 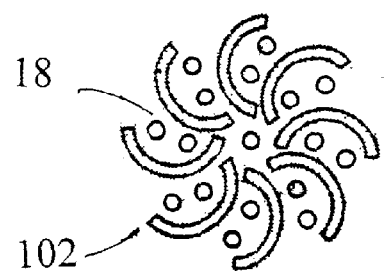 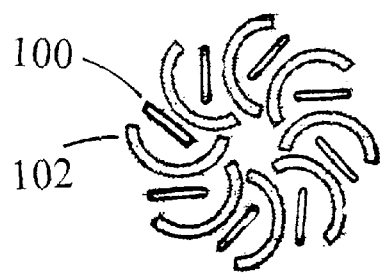
FIG.17    FIG.18    FIG.19
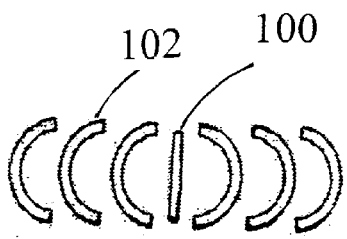 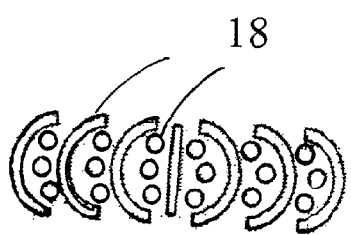 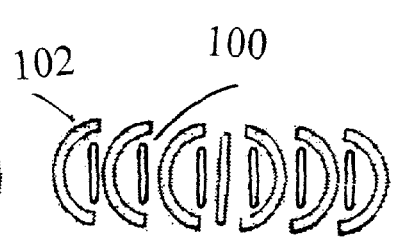
FIG.20    FIG.21    FIG.22

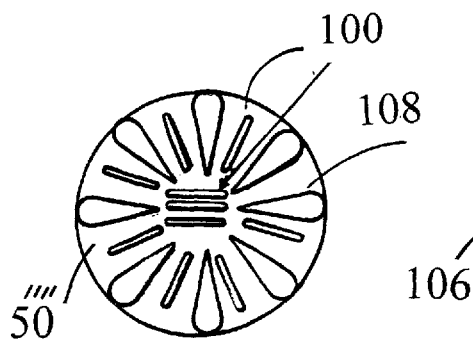
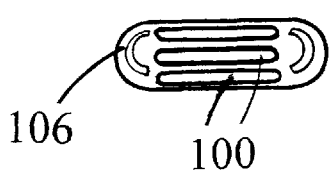
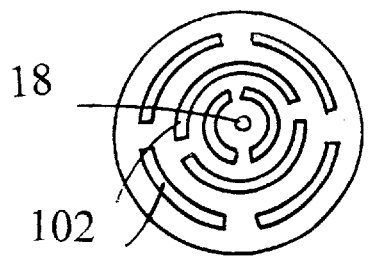
FIG.23   FIG.24   FIG.25
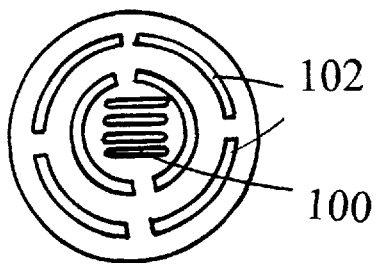
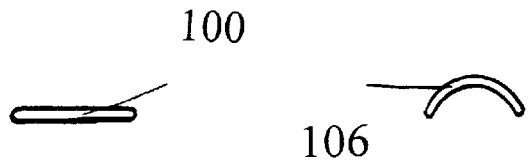
FIG.26   FIG.27   FIG.28
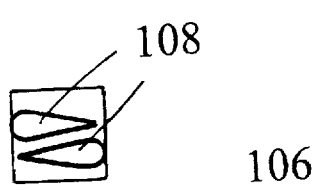
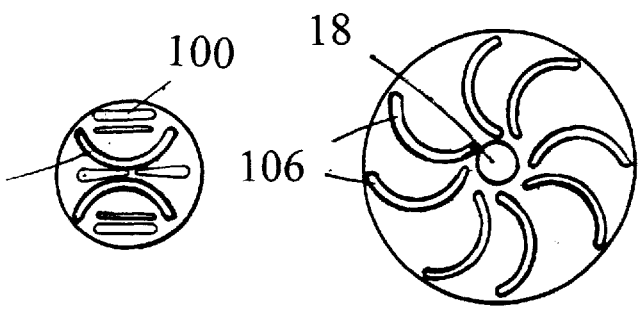
FIG.29   FIG.30   FIG.31

MULTIPLE MICROCHANNELS CHIP FOR BIOMOLECULE IMAGING

CROSS REFERENCE DATA

This application is a Continuation-In-Part patent application of co-pending parent patent application Ser. No. 09/634,709 filed on Aug. 7, 2000.

FIELD OF THE INVENTION

This invention relates to providing a microchannel chip device which will be able to perform a large number of bio molecule tests simultaneously, as well as producing a uniform test environment for each biomolecule test and eliminate the statistical test to test variations.

BACKGROUND OF THE INVENTION

It is known in fluid dynamics that, due to the viscosity of the biological sample containing fluid, which is usually water, the dynamic pressure to pass this fluid through and into the multiple channel glass panel increases as the microchannel diameter is reduced and the glass plate thickness increases. Threshold values are such that, below $10\mu$ in channel diameter, increase in vacuum pressure is required to force water through the microchannels, and also structural integrity of the glass sample then becomes problematic. However, on the other side, by increasing channel diameter beyond $10\mu$ and reducing the thickness of the glass plate, vacuum pressure is still required but to a lesser extent, while undesirable artifacts are generated in particular increased diffuse halos around the top access mouth of the channels. These undesirable artifact halos considerably deteriorate both the image quality and the sensitivity of the test.

It is noted that fluid dynamics in a microchannel are not the same as those in diametrally larger tubes, e.g. a water filled coffee mug. Indeed, because of the larger inner diameter of a coffee mug, when a water filled coffee mug is tilted from an upright condition to a laterally inclined position, the top surface menisk of the volume of water will not concurrently tilt and thus will remain parallel to the ground in both instances, although the longitudinal axis of the mug is no longer vertical in its tilted condition. On the other end, due to surface tension properties and viscosity of the water and due to the micrometer grade diameter of the microscopic (micro-) channel, when a microchannel is tilted from an upright condition to a laterally inclined condition, the menisk will not stay parallel to the ground as it did in larger diameter cylinder such as a coffee mug, but will tilt with the tilted microchannel so that the perpendicular axis to the top surface menisk of the water volume inside the tilted microchannel will remain coaxial to the longitudinal axis of the tilted microchannel.

Existing devices for binding a target molecule comprise a substrate having a multiplicity of discrete tubes extending transversely therethrough. These tubes extend orthogonally to the top surface of the substrate. A first binding reagent is immobilized on the walls of a first group of tubes, while a second binding reagent is immobilized on the walls of a second group of the tubes. Such device is for use in the identification or characterization of nucleic acid sequences through nucleic acid probe hybridization with samples containing an uncharacterized polynucleic acid, e.g. recombinant DNA, polymerase chain reaction fragments, etc . . . as well as other biomolecules.

In these known tubes, their diameter ranges between about 0.03 to $10\mu$. The reason for the top threshold diameter value is that if your have upright tubes or channels, any diameter larger than about $10\mu$ will enlarge optical halo artifacts at the top access mouth of the tubes, and accordingly will bring, much reduced sensitivity.

During the 1990s, microfabrication technology has enabled miniaturization and automation of manufacturing processes in numerous industries. The impact of microfabrication technology in biomedical research can be seen in the growing presence of microprocessor controlled analytical instrumentation and robotics in the laboratory engaged in high throughput genome mapping and sequencing (see the current "Human Genome Project", with its first phase just completed). Optical detection of fluorescent labelled receptors is employed inter alia in detection for sequencing. Detection can be achieved through use of a charge coupled device array, or confocal laser imaging technology such as DNA scope (TM).

Capillary tube glass arrays are already in use as high surface area nanoporous support structures to tether DNA targets or probes for hybridization. Such capillary tube glass wafers contain a regular geometric array of parallel holes or tubes as small as 33 nanometers in diameter, or as large as several micrometers in diameter. These holes or tubes serve as sample wells for placement of a substantially homogeneous sample of a biomolecule within each hybridization site. The orifices are fabricated using excimer laser machining.

However, such prior art microscopic detection devices usually require charged coupling devices, and cannot scan the full sample area. This is because, since you have vertical micro-channels, the diameter thereof larger than $10\mu$ will produce much larger optical halo artifacts and will bring about much diminished microscopic sensitivity. This is why the claimed microchannel diameter in the Beattie patent is limited to a range from 0.03 to $10\mu$.

Methods are also known in the art for delivering subnanoliter microdroplets of fluids to a surface at submicron precision. A microjet system or a microspotter, capable of delivering subnanoliter DNA solution to the wafer surface, can thus be employed.

Moreover, in the field of biotechnology, there is an increasing use of biochips for detection of macromolecules such as DNA and proteins. Amongst the various numbers of biochips the flow-through bio-chip is preferred, because of the advantage in terms of speed of the reaction and sensitivity associated with it. Mostly these biochips are made from cylindroid and cross-sectionally polygonal channels that are extended through the length of the panel chip. The diameter of these channels may vary from a few to several hundred micrometers, but usually about $25\mu$.

Most of the testing solutions such as serum, are not homogeneous in nature and contain impurities as the entire cell or cell particles. Some are very viscous in nature and have difficulties passing through small pores of micrometer size. Serum contains fibrin, which is the long strands of wire mesh adapted to entrap the cells. These fibrin strands may be present in serum even after separation. Other impurities like leukocytes with a diameter of $35\mu$ and thickness of a few micrometers, may clog the cylindrical pore. If the pore is in the shape of a slot with a length of e.g. $40\mu$ and a width of $3\mu$, it thus has opening area of 120 square $\mu$ which can easily accommodate the passage of white blood cells (WBC) through the panel chip. Cylindrical pores with a diameter of $40\mu$ have opening area of $(20\times20\times3.141592\mu)$ or approximately $1,256\mu^2$, being ten times bigger than the slot form.

Indeed, the bigger the diameter of cylindrical channels, the worst image deterioration occurs in scanning. The opening area and dead space may be interchangeable terms. Usually, opening area is the area of open space (or empty space) that extends through the chip from the surface or the surface area which separates these channels. The inner surfaces of these pores are areas in which most binding occurs. A cylindrical pore with diameter of $2\mu$ and a constant thickness K has opening area of $(1\times1\times3.141592)$ or approximately 3 square micrometers with inner surface area of $(2\times K\times3.141592)$ i.e. approximately 6K or 6. Since both panel chips have the same thickness, so the K would remain the same. If one increases the diameter of a cylindrical pore to $200\mu$, the opening area would be $(100\times100\times3.141592)$ i.e. approximately 30,000 square micrometers, and inner surface would be $(200\times3.141592)$ i.e. approximately $600\mu^2$. From these calculations it is understood that 100 folds increase in diameter of cylindrical pore shape from 2 to $200\mu$, has resulted in a 10,000 times increase in opening area (from 3 to 30,000) which is considered to be useless area where no binding occurs, and 100 times for inner surface area (from 6 to 600) where the binding occurs and is considered to be the useful area.

The increase of this opening area or useless area which occupies empty space, will compromise the structural integrity of panel chips and make it more prone to breakage and deterioration of image quality. It also contributes to building of arrays of lesser density, since less if not any empty spaces will remain in the chip. If a pore is in the shape of a slot such as rectangle with the length of $10\mu$ and width of 2 microns and the thickness of K, it has opening area of $(10\times2)$ i.e. 20 square micrometers, and the inner surface area of $(10+10+2+2)$ i . . . 24K, or $24\mu^2$ as K stays constant. If the length of slot increases to 200 from $10\mu$, while keeping the width constant at $2\mu$, the opening area would be $(200\times2)$ i.e. 400 square micrometers, and the inner surface area of $(200+200+2+2)$ K i.e. $404\mu^2$ (K is the thickness of panel chips and stays the same).

Therefore, 20 folds increase in length of slot from 10 to $200\mu$, in order to accommodate the passage of the larger particle size through the channel such as the cell, and viscous solutions has resulted in 20 folds increase in opening area or useless area where no binding occurs (from 20 to $400\mu^2$). At the same time, the inner surface area where the binding occurs and is considered as useful area, has increased approximately 17 times (from 24 to $404\mu^2$). This clearly demonstrates the superiority of slot form channels over other classical cylindrical shape pores, wherein in slot channels, the ratio of inner surface of channels (useful area) to open area (useless area) stays the same (17/20) compared to (100/10,000) in cylindrical pores, in which there is a one hundred times increase in useless area. But since there is also more slot channels FIG. 16 (100 and 104) in a given area than one single cylindrical channel, therefore, more inner surface area is available for molecule to bind to. Thus, the more intense the image would be.

Therefore, in pores with cylindrical shapes, this drastic exponential increase in ratio of useless area (where no binding occurs) to useful area where binding occurs in order to accommodate the passage of larger particles and cells through the channels, is detrimental and generates limiting factors in increasing the pore size of cylindrical forms, and also incorporates more empty space into the panel chip. This limiting factor to enlargement of cylindrical pores is a contributing factor in blocking of pores and more assisted vacuum control. Any attempt to ignore this limiting factor and build the larger pores, leads to exponential increase in ratio of empty space to useful area and contributes to image deterioration and undermines the structural integrity of the chips. On the contrary, the slot forming channels do not have this negative impact in size enlargement and are capable of acting as wave-guide to carry the fluorescent excited light from the inner area to the surface, while allowing the passage of larger particles and impurities and more viscous solutions. The slot forming channels provide maximum binding inner surface area per pixel, compared to cylindrical pores, and therefore do not contribute to empty space as much as cylindrical pores where there is more inner surface per pixel, so more binding occurs. Therefore, each pixel shows more intensity in slot channels.

OBJECTS OF THE INVENTION

An important object of the present invention is therefore to improve upon the above-noted prior art technology, by providing a device which will be able to perform a large number of bio molecule tests simultaneously, as well as producing a uniform test environment for each biomolecule test and eliminate the statistical test to test variations.

A further important object of the present invention is to use the capillary tube as an environment that can produce an internal reflection known as "pipping effect", so as to increase sensitivity and resolution of biomolecule detection.

Still another object of the invention is to use the capillary tube as an environment in which samples and reagents flow through, to increase the interactions between biomolecules so as to reduce the incubation time and increase the sensitivity and resolution at the same time, to thus enable use of a more diluted sample for the same efficiency.

An object of the invention is to provide a structure suited for making a device for binding macromolecules while allowing the passage of other impurities to prevent clogging of pores and further facilitating flow-through of solution to be tested.

An important object of the present invention is to provide a large variety of different patterns and shapes of channels layout through the thickness of the microchip, in each unit cell, so as to enable matching of channels layout with the shapes of microscopic impurities in testing solutions.

A further important object of the present invention is to provide a better flow for more viscous solutions in microchip channels, by increasing the length of channel slots while keeping the width to a minimum.

Another object of the invention is to provide slot channel shape generating a maximum binding environment within a minimum opening area. This will result in increase in the number of molecules binding per pixel, since more inner surface is available which increases the intensity of pixel and provides better sensitivity.

An important object of the invention is to provide a sharper and more uniform microchip channel imaging. This will improve the dynamic range in greater detail, and provide better distinction between positive and negative spots and leave less to guesswork.

A general object of the invention is to reduce labour costs and required effective sample volume associated with operation of such devices.

SUMMARY OF THE INVENTION

According to the invention, there is disclosed a rigid panel chip for supporting biological samples for observation with a microscope, said glass panel defining a top flat surface, a bottom bearing surface, and a plurality of unit cells extending generally parallel to each other from said top to bottom surfaces, each of said unit cells defining a layout at said top surface of at least two channels arranged in plan view generally symmetrically relative to one another, each of said channels defining a top access mouth for ingress of said biological samples and having such an inner diameter as to accommodate flow through viscosity of a biological sample containing fluid;

wherein a sharper and more uniform panel chip channel imaging is achieved.

Preferably, the number of said channels in each of said unit cells can vary between about two and thirty.

The substrate for fabrication of the panel chip may be selected from polymers, plastics, polypropylene, parylene, polyester, polyimide, polyurethane, synthetic resins, polyethylene, polystyrene, glass, silicon dioxide, fused silica, borosilicate, metal, and aluminum.

Said channels layout at said panel top surface in a given unit cell could be selected from:

at least three straight slot channels, extending parallel to one another;

an air fan like layout of arcuately shaped "blade" channels, with a central circular "hub" channel forming the top end of a cylindroid channel;

a number of concentrically disposed arcuate channels, with a central circular channel forming the top end of a cylindroid channel; and a number of cross-shaped disposed straight channels.

Preferably, said channels layout at said panel top surface in a given unit cell includes a number of star shaped disposed straight channels. A pair of straight channels may be added, being much shorter than said star shaped disposed channels and disposed parallel to one another centrally of said star shaped disposed channels. A plurality of circular channels could be disposed concentrically of said star shaped disposed channels and forming the top end of cylindroid channels. A plurality of additional shorter straight segments channels could each be disposed concentrically of said star shaped disposed channels in between a pair of successive said star shaped disposed channels but at a distance from the center of the unit cell.

Alternately, said channels layout at said panel top surface in a given unit cell could include a number of C-shaped channels successively disposed circumferentially thereof in the same trough-facing circular direction. A number of circular channels could then be disposed within said C-shaped channels and forming the top end of cylindroid channels. A plurality of shorter straight segments channels could also be disposed within said C-shaped channels.

Again alternately, said channels layout at said panel top surface in a given unit cell may include a pair of triplets of C-shaped channels disposed in facing opposing register relative to one another. A plurality of circular channels could be sparsely settled about said C-shape channels and forming the top end of cylindroid channels.

Alternately, a plurality of shorter straight channels could be sparsely settled in between each pair of successive C-shape channels.

Said channels layout at said panel top surface in a given unit cell could rather include a plurality of radially extending waterdroplet like channels.

Said channels layout at said panel top surface in a given unit cell could also include a few waterdroplet like channels, disposed parallel to one another.

In a more general sense, the invention could also be directed to a rigid panel chip for supporting biological samples for observation with a microscope, said glass panel defining a top flat surface, a bottom bearing surface, and a plurality of unit cells extending generally parallel to each other from said top to bottom surfaces, each of said unit cells defining at least one slot channel, said channel defining a top access mouth for ingress of said biological samples and having such an inner diameter as to accommodate flow through viscosity of a biological sample containing fluid; said slot channel having a shape selected from a straight slot, an arcuate slot and a water droplet like slot;

wherein a sharper and more uniform panel chip channel imaging is achieved.

BRIEF DESCRIPTION OF THE DRAWINGS

FIG. 10A is a partly broken enlarged perspective view of a corner section of an alternate embodiment of micro-chip according to the present invention, showing in a single cell unit four rectangular slit channels disposed side by side;

FIG. 10B is a plan view of the slit channels quadruplet of FIG. 10A;

FIGS. 11A and 11B are views similar to FIGS. 10A and 10B, respectively, but for another embodiment of now spider shape channels layout;

FIGS. 12A and 12B are views similar to FIGS. 10A and 10B, respectively, but for still another alternate embodiment of now multiple arcuate channels segments layout;

FIGS. 13A and 13B, 32A–32B, and 33A–33B, are views similar to FIGS. 10A and 10B, respectively, but for three other embodiments of cross-shape channels layout, cylindroid funnel shape channel layout, and rectangular funnel shape channels layout, respectively; and FIGS. 14 to 31 are plan views of various other alternate channels layout for a micro-chip.

DETAILED DESCRIPTION OF THE PREFERRED EMBODIMENT OF THE INVENTION

Figure 1:
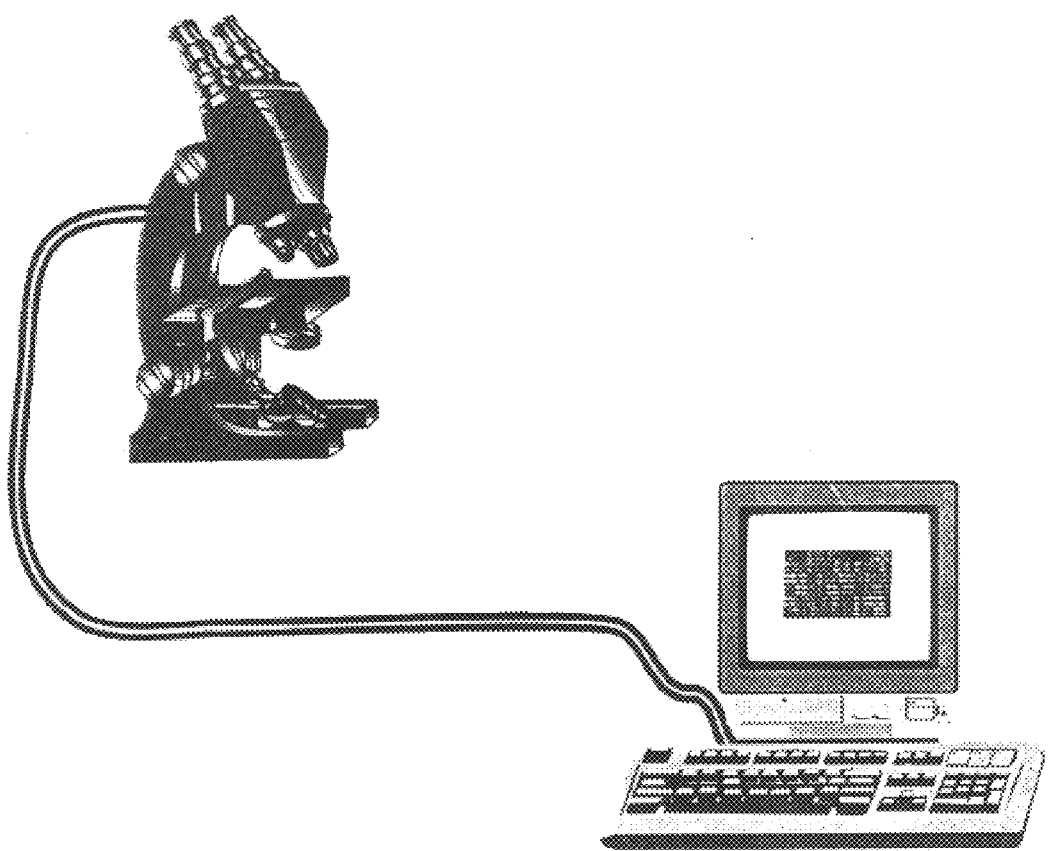
FIG. 1 is a schematic perspective view of a prior art microscope and computer system assembly, coupled to a CCD unit for observing a sample supporting glass plate.
Figure 3:
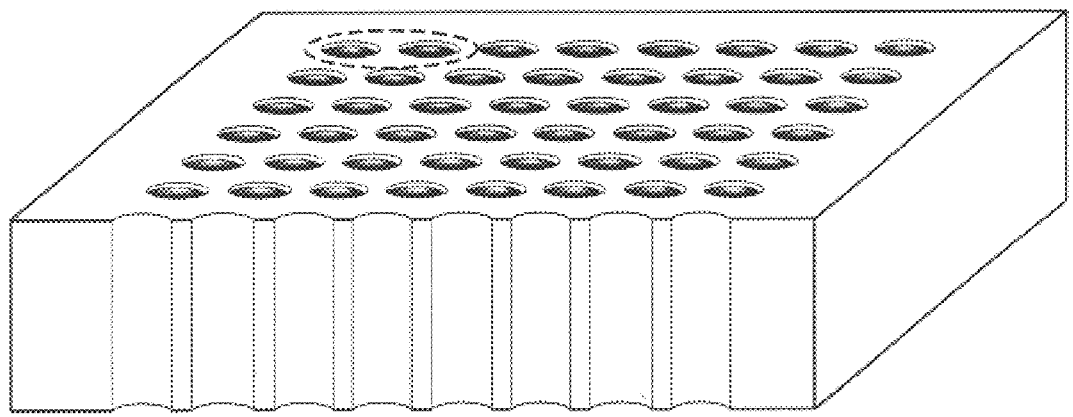
FIG. 3 is an enlarged partly broken isometric and sectional view of a prior art microchip showing that the channels are orthogonal to the chip top surface.
Figure 5:
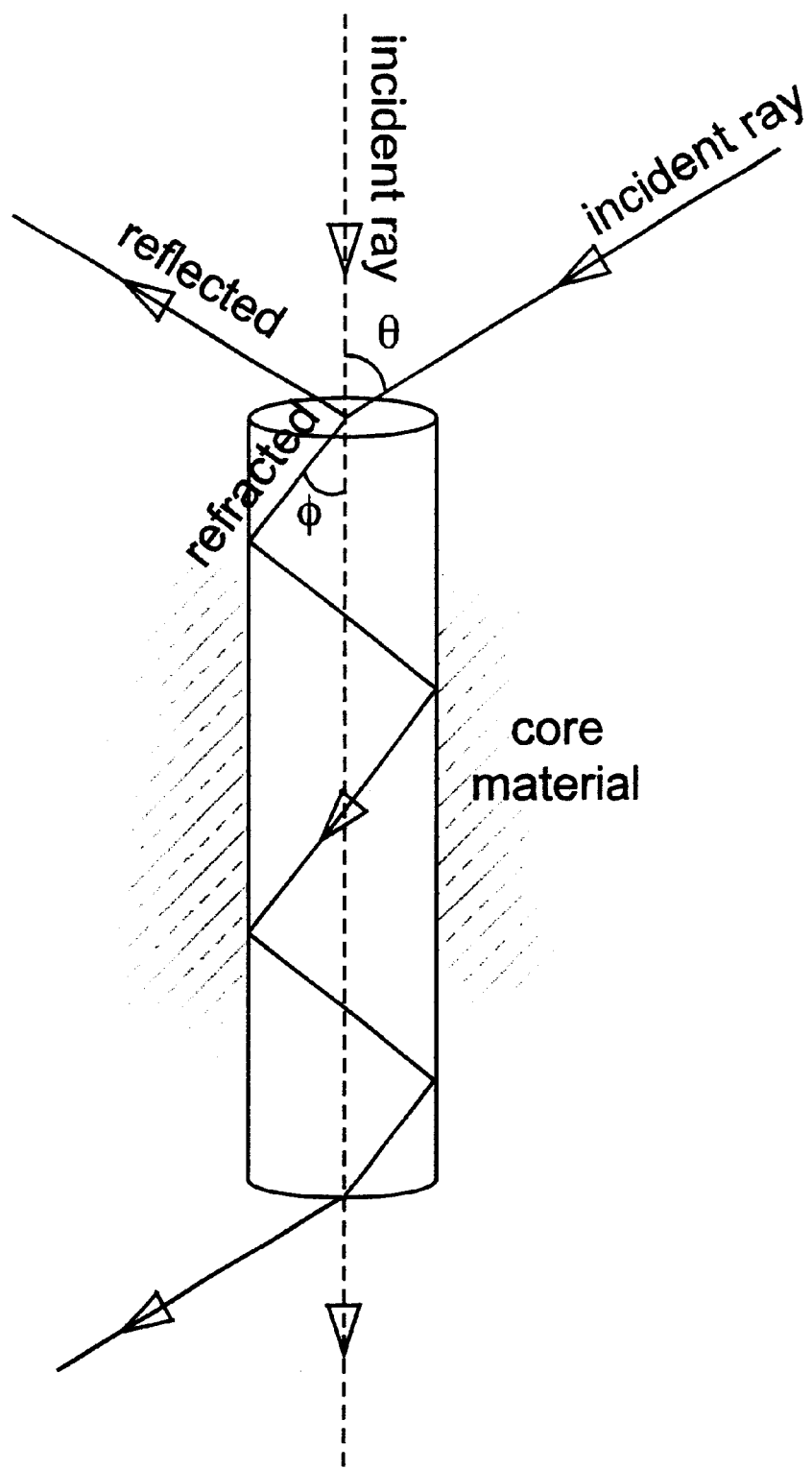
FIG. 5 is a schematic view of a single straight prior art micro-channel similar to those in FIG. 3, showing that the light cannot enter the microchannel entirely without losing its power to reflection and also suggesting that when the laser beam is directed perpendicular to the surface, it enters the micro-channel and exits from the other end without producing total internal reflection.

FIGS. 3 and 5 of the drawings show prior art microchannels. Each such microchannel is a regular array of the unilength type in perpendicular position to the surface of the plane. It is vertical or upright, inside the glass observation plate. This microchannel is of uniform length and shape, and is vertical. As further shown in FIG. 1, it needs to be scanned through the entire length of the channel for detection, it requires special scanning device, and is therefore expensive. It has average emission excitation, a cross-talk, and a halo circle around the top sample access end mouth constituting an artifact. It has average to low sensitivity. Its maximum operational diameter is 10μ or less. It further needs seals and vacuum pressure to engage the water sample inside the microchannel, due to the microchannel diameter being too small for unassisted engagement.

Figure 3A:
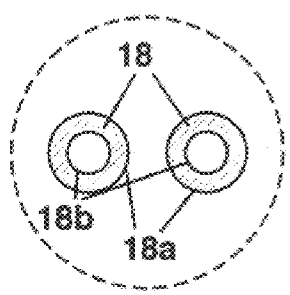
FIG. 3A is a top end view of two adjacent channels from the top chip surface of FIG. 3.

As is shown in prior art FIG. 3A, there is a top end view of two adjacent channels when looking from top through the microchannels. Element 18a represents the top opening of the first channel, and element 18b represents the bottom opening of the same channels. Element 18 is the inner wall of the microchannels.

When one increases the diameter of the channels from 2 to 200μ, i.e. by two orders of magnitude, the inner surface of the channel will increase by 200 divided by 2, i.e. by 100 times, by the surface area of the black hole. In the prior art system of FIG. 3A, the increase is of 10,000 times, i.e. by four orders of magnitude. This will therefore be a critical factor in deterioration of the image quality which prevents the inner diameter in the channel in FIG. 3A to be operative more than about 10μ. This is shown in the following calculation in FIG. 3A:

18b=2μ (channel diameter)
area of inner wall 18 (FIG. 3A)=2π×H, where H is the height
area of opening of each channel: 2/2×2/2×π=π (no unit used)
18b=200μ of channel diameter
area of inner wall 18 FIG. 3A: 200π×H
area of opening of each channel=200/2×200/2×π=10,000π (no unit used)

We can see that a one hundred time set increase in inner wall surface area 18 FIG. 3A, has resulted in 10,000 time (exponential) increase in black hole artifact 18b (FIG. 3A). But this is not the case in the present invention, as illustrated in FIG. 4A, since there is no black hole or halo artifact represented when the diameter of channels increases from 2 to 200μ. In the black hole or halo artifact of the prior art 18b (FIG. 3A), there is lack of flurorescent glow, when it is viewed from top position and this gives a dark and halo like appearance in image capturing.

Moreover, inspection of light imaging in prior art FIG. 3A is performed through tedious multiple scanning of transverse strata along the full length of a chip microchannel, contrary to the surface scan of the present invention at FIG. 4A.

Figure 2:
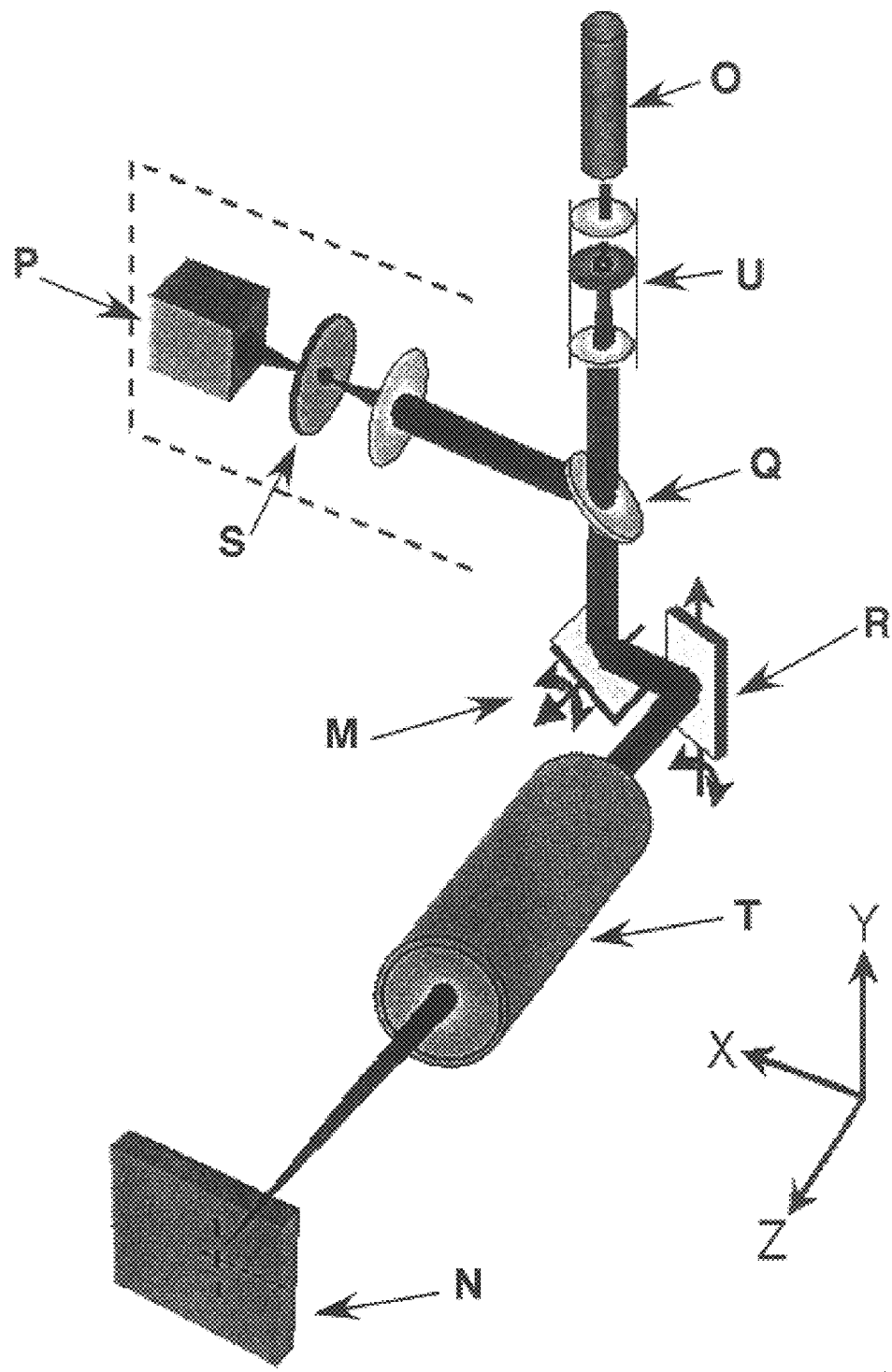
FIG. 2 is a schematic perspective view of a confocal imaging system for surface inspection on a specimen holder of a microchip according to the present invention.

FIG. 2 alternately shows a confocal imaging system for use with the chip of the present invention. System M includes a specimen holder N, for supporting the sample containing chip, a laser gun O for beaming light onto the specimen holder, and a black hole light detector P, for imaging the biomolecules inside the chip channels. A beam splitter Q and tilted mirror assembly R, is mounted intermediately of the specimen holder, light detector and laser gun. A pinhole member S is mounted between the light detector and beamsplitter. A laser scan lens T is mounted between the specimen holder and the scanning mirrors. A spatial filter and beam expander, U, is mounted between the laser gun and the beamsplitter.

In FIG. 2, the beamsplitter allows both free laser beam passage from gun O to specimen holder N in a first direction, and return passage of the biomolecule imaging beam from the specimen holder to the detector P through reflection against intermediate beam splitter Q. The light detector should be coupled to a suitable microscope, for example a microscope having parfocal arms and submicron diffraction limited resolution with 12 or 16 bit dynamic range detection, such as for example sold under the MACROSCOPE or DNAscope trademarks by BIOMEDICAL PHOTOMETRICS inc. (Waterloo, Canada).

Figure 6:
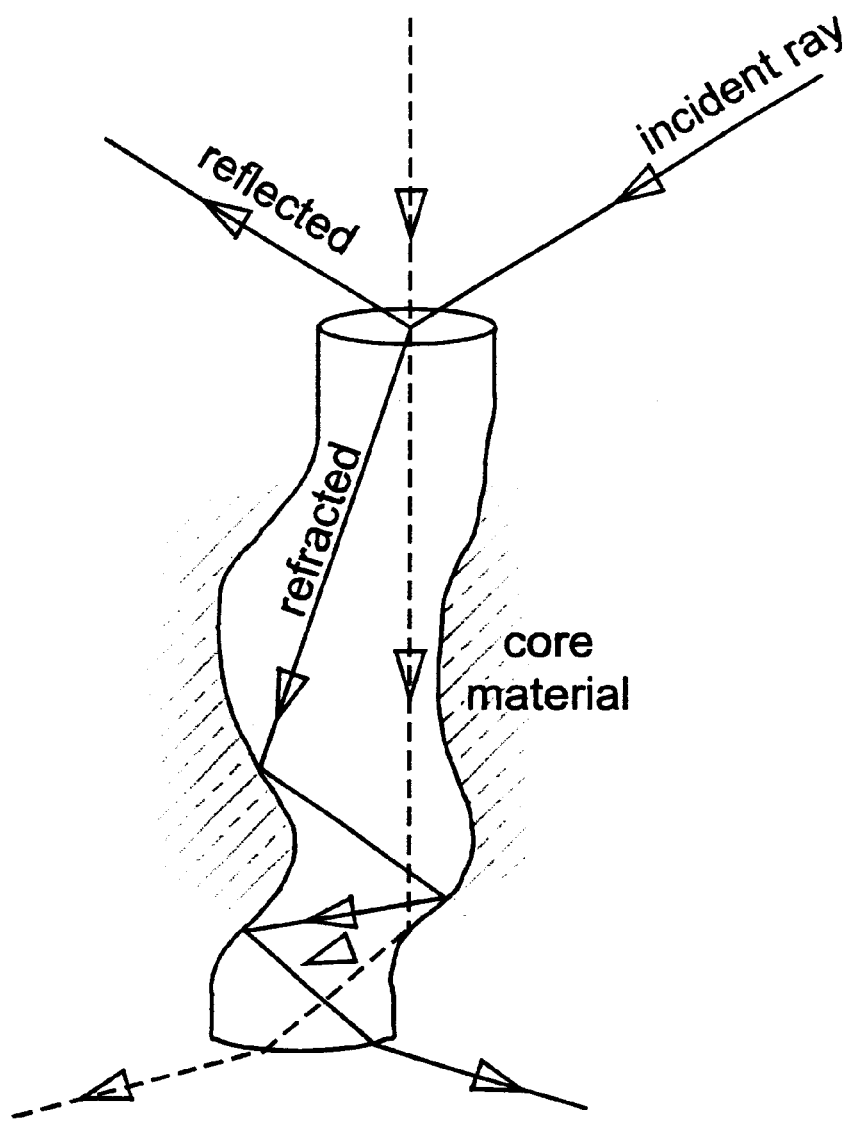
FIG. 6 is a schematic view of another isolated prior art irregularly shaped microchannel, suggesting how light can not enter entirely into the channel without having some being reflected, this nanoporous silicon with non uniform inner wall showing scattered internal reflection which contributes to an increase in cross-talk and light escaping from the micro-channels.

FIG. 6 of the drawings shows an alternate prior art microchannel. This porous silicon nanochannel, which has a diameter of less than 1 micrometer, i.e. about 0.03μ, is an irregularly shaped array of variable length and size. It is of non uniform size and length. Its level of excitation emission is minimal. It has maximum cross-talk. Again, it has a small inner diameter of less than 1 micrometer, meaning once again that for engagement of sample fluid therein, high vacuum pressure is required, which results in compromising the structural integrity of the chip. Also, various sample fluid quantity is bounded due to varying length and non uniformity.

Figure 4:
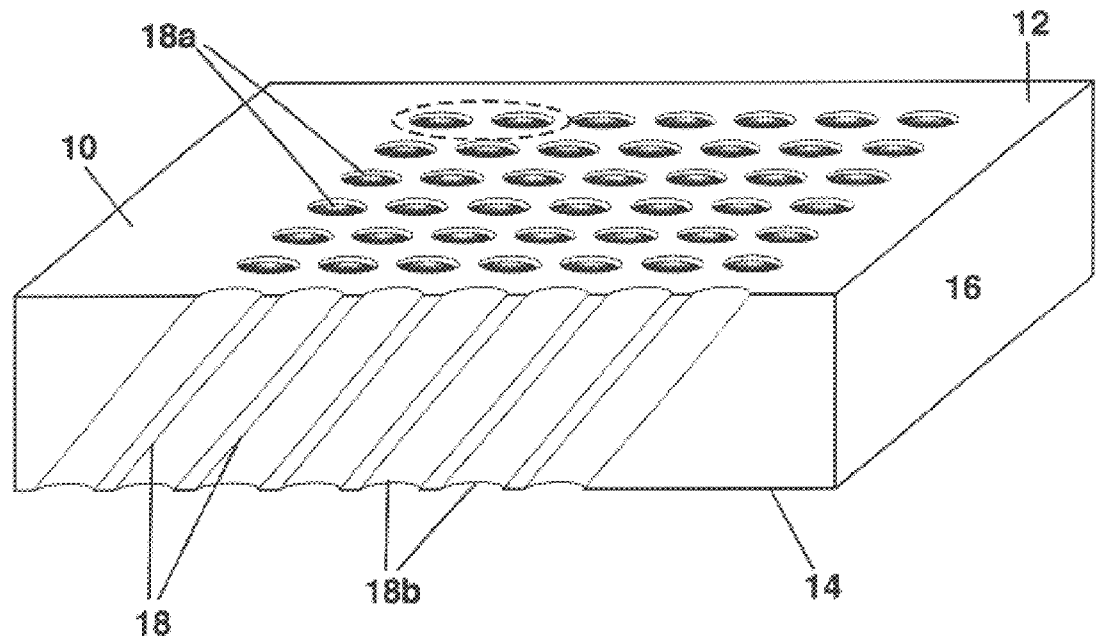
FIG. 4 is an enlarged partly broken isometric and sectional view of the multiple channel glass plate of the invention, showing the slant of the oblique channels made through the thickness of the glass plate chip.
Figure 4A:
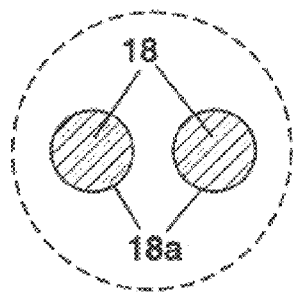
FIG. 4A is a view similar to FIG. 3A but for the present invention chip, and suggesting that the observer has no direct line of sight between the top and bottom ends of each through micro-channel.
Figure 7:
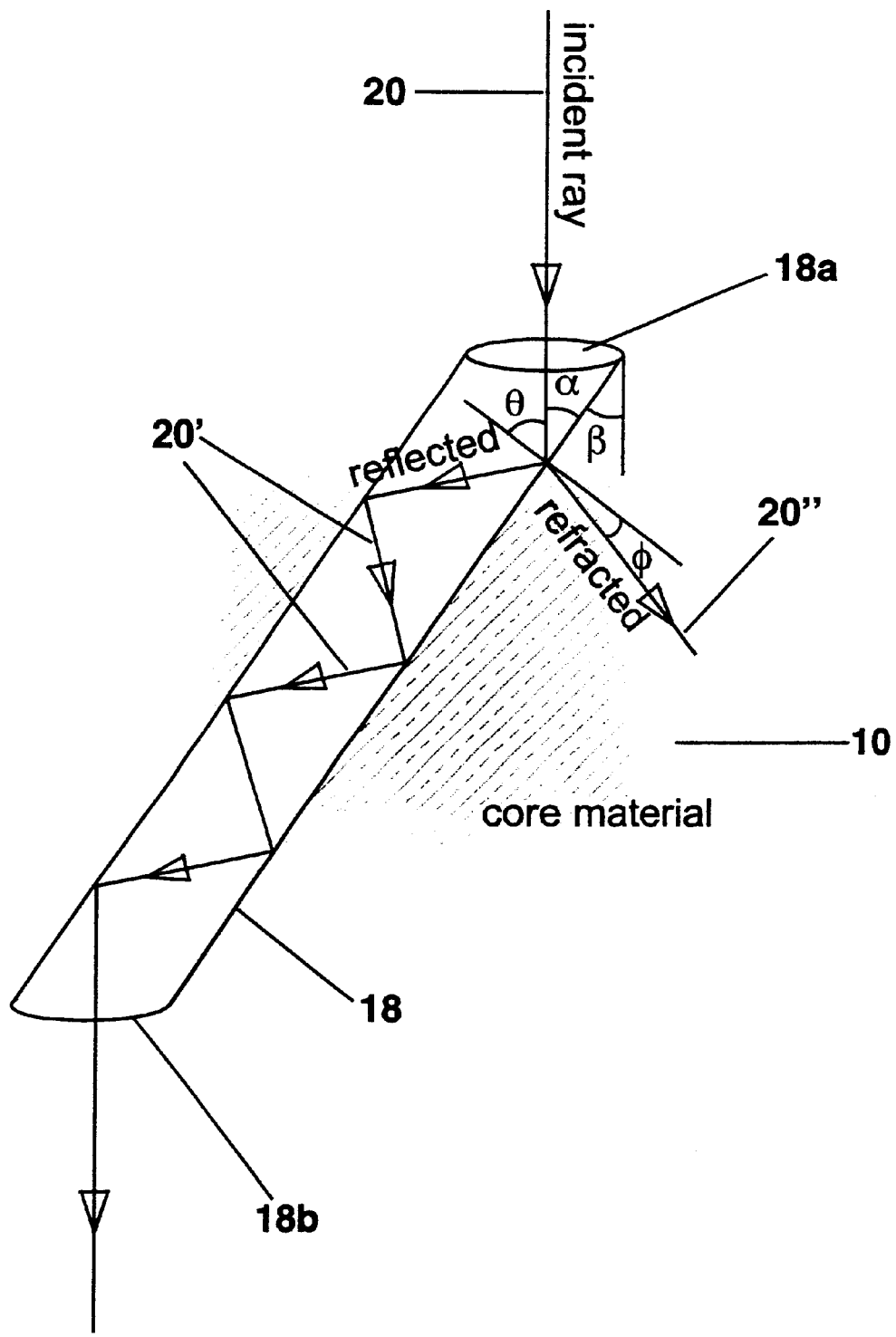
FIG. 7 is a view similar to FIGS. 5 and 6, but showing the preferred embodiment of slanted channel inside the glass panel chip according to the present invention.

FIGS. 4 and 7 show a micro-channel 10 according to a preferred embodiment of the present invention. The glass plate 10 defines top and bottom flat surfaces 12, 14, respectively, being parallel to one another, spaced by a full thickness glass body 16. The present invention microchannel forms a regular array of uniform length microchannel tubes and extends along a pre-established constant angular orientation. More particularly, the hollow microchannel 18 extends obliquely relative to an axis perpendicular to both top and bottom flat surfaces 12 and 14. The bottom flat surface 14 is the bearing surface of the glass plate. The top mouth 18a of the microchannel 18 is coplanar to the top flat surface 12 of the glass plate, while the bottom mouth 18b of the microchannel 18 opens at the bottom flat surface 14 of the glass plate. The microchannel is of uniform throughout length, and provides an oblique fluid flow through. This microchannel can use CCD (charged coupling device), PMT (photomultiplier tube) or flat surface laser scanners, for biological sample detection. It has maximum emission excitation. It has minimum cross-talk. Most importantly, no artifact halo circle is generated at the top mouth 18a, where observations are performed preferably by a flat surface laser scanner. The present invention microchannel has maximal internal reflection and maximal sensitivity features. It is a larger microchannel diameter than the prior art ones, bringing about less plumbing problems. Since detectors P are placed on top of channels, the light which exits the channels are in vertical column and parallel to each other without having the blackhole in the center.

In the present invention microchannel, the obliqueness thereof relative to the glass panel top surface, forms a fixed angular value being computed from Snell's law:

$$n1 \sin \theta = n2 \sin \phi$$

with the refractive index of air being by definition 1, of water, 1.33, and of glass, ranging between 1.41 to 1.61 (with an average of 1.51) depending on the manufacturer.

As is known from college level physics, Snell's law is a law of geometric optics, that defines the amount of bending that takes place when a light ray strikes a refractive boundary. Where n1 is the index of refraction of the medium in which the incident ray travels, θ is the angle with respect to the normal at the refractive boundary at which the incident ray strikes the boundary, n2 is the index of refraction of the medium in which the refracted ray travels, and φ is the angle with respect to the normal at the refractive boundary at which the refracted ray travels. If a ray travels from a medium of lower refractive index into a medium of higher refractive index, it is bent toward the normal. If it travels from a medium of higher refractive index to a medium of lower index, it is bent away from the normal. Total internal reflection occurs when light, in a higher refractive index medium, strikes an interface with a medium with a lower refractive index, at an angle of incidence (with respect to the normal) greater than the critical angle. This reflection occurs even in the absence of a metallic reflective coating (e.g. aluminum or silver).

This microchannel obliqueness critically enables the laser light beam to penetrate the sample containing fluid inside the microchannel at its maximum strength.

For calculating the oblique angle β of the microchannel, i.e. the angle between the longitudinal axis of the microchannel and the axis perpendicular to the top surface of the glass panel into the thickness of which the microchannel is nested, this is based on the properties of the glass material and the refractive index:

$$\alpha + \beta = 90°$$

$$\beta + \theta = 90°$$

$$\beta = 90 - \theta$$

The incident ray of the laser beam is perpendicular to the top surface of the sample glass plate, so the laser beam penetrates to the maximum without any undesirable reflection; that is important since the stronger the beam, the more fluorescein dyes within the channel will be excited.

As suggested in FIG. 7 of the drawings on file, once the laser beam 20 hits the glass side wall of the channel tube, it produces both reflected beams 20' and refracted beams 20". If angle θ has a value of 90 degrees, it is parallel to the side of the glass core, and remains inside the channel tube. If on the other hand angle θ has a value of zero, then the light will exit the channel tube. The critical angle is chosen where the maximum internal reflection is to occur and minimum light is to escape from the tube 18. This critical angle is important because if the angle is less than this value, some light goes through the chip glass core and escapes from the light channel tube 18.

Let's assume that the critical angle for a glass material with refractive index of 1.46 is equal to 44°. The oblique angle β=α=90−44=46. This oblique angle is set to produce the maximum total internal reflection and the minimum loss due to refracted beam.

Alternately, the chip could be made from non-transparent material. Then, the microchannel 18' should be lined with an inner light reflecting coating 18a', preferably made from a metallic material selected from the group comprising aluminum and silver. In this format, this alternate embodiment of chip 10' need not be transparent. The channels still remain in oblique flow shape but there is a reflective metallic coating 18a' (see FIG. 8). This metallic coating will usually be aluminum, having an average of 90% reflectivity between 200 and 1000 nanometers. Also, vacuum deposition of several other metals makes excellent reflectors. The protective monolayer 22 in FIG. 8, shields layer 18a' from oxydation that can be a deposit of silicon (SiO2) or magnesium fluoride (MgF2) or other, to insure high reflectance from the UV to the infrared range. The oblique flow shape of the micro-channels help to ensure that the maximum level of light penetrates and exits from the microchannels. Since the inner channels are coated with reflective material, the light does not escape to the core material and exit at its maximum. Therefore, there is no Snell's law or critical angle, but only an oblique angle.

We will now address the present invention oblique flow technology. Although flow through chip known as the three dimensional chip has many advantages over the flat surface chip, there are nevertheless major inherited problems with the nature of these chips that make them highly undesirable and economically unattractive. These problems include:

plumbing;

detection; and use of expensive microscopy and devices that can scan the length of the channel, for detection.

On the other hand, with oblique flow technology, there is a new class of three-dimensional gene chip that has addressed these problems.

With the plumbing problem, the pressure required to pass liquid through the top access mouth of the microchannel, increases as the microchannel diameter is reduced and the glass plate thickness is increased. More particularly, as the prior art microchannel inner diameter decreases below $10\mu$ (micrometer), there is required a higher vacuum pressure level and it becomes problematic in maintaining structural integrity of the chip. On the other hand, by increasing the micro-channel diameter and reducing the glass plate chip thickness, undesirable artifacts are generated including diffuse optical halos around the top access mouth of the microchannel. This halo artifact will deteriorate the image quality of the laser surface scanner, hence the lateral intensity comparison of different micro-channels. Also, by reducing the channel diameter and increasing the number of channels, the structural integrity of the chip will be compromised.

Figure 9:
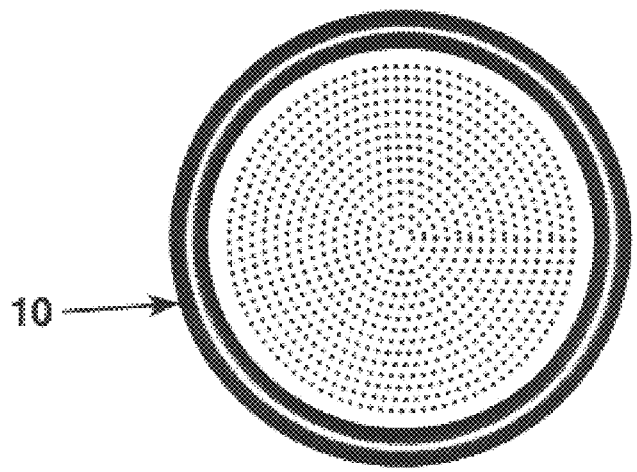
FIG. 9 is a top end view of an alternate embodiment of circular chip of the present invention.
Figure 9A:
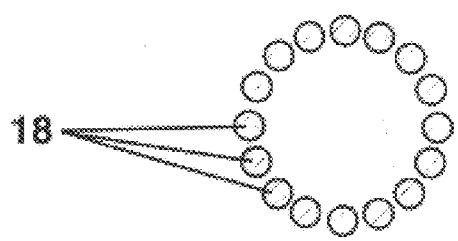
FIG. 9A is an enlarged top end view of a central portion of the circular chip of FIG. 9.
Figure 9B:
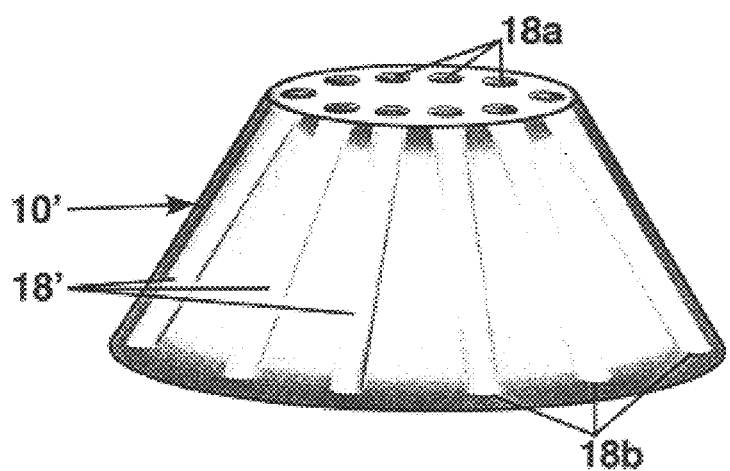
FIG. 9B is an elevational view of still another alternate embodiment of chip, having a conical shape with the channels disposed in an upwardly radially inwardly inclined peripheral fashion, for use in a centrifuge rather than with a vacuum assist means for the filling and drainage of the biological specimen liquid from the micro-channels.

Alternately and as illustrated in FIG. 9B, the chip instead of being rectangular (as in FIG. 4), may be conical or circular in shape. The array of micro-channels 18' would then be disposed in an upwardly, radially inwardly inclined fashion. With such an alternate chip 10', the power assist means for drainage and filling of the micro-channels 18' with the biological sample solution, instead of being small vacuum assisted means, can be replaced by a centrifuge. The centrifuge may operate e.g. at 2500 RPM for about 2 minutes, to allow the biological sample solution to engage and settle inside the micro-channels. It is noted that such centrifugal technique for filling the chip oblique microchannels with biological sample solution, would not be effective in the prior art chips having vertical (non-oblique) microchannels. Indeed, in the prior art chips, the liquid inside the microchannels cannot be drained off from the bottom, contrarily to the case with oblique angle micro-channels according to the present invention. The spotting of material on a conical chip is also easier than on a rectangular chip. Imaging detection can be less bulky, since the scanning could be facilitated by the circular motion of circular disk along its center. A hand held and portable device is achieved from afforded size reduction. These are critical differences compared with prior art techniques, generating unexpected results.

As for the detection problem, most prior art microarrays are produced on microscope slide glass, where the binding reaction and signal generation occurs within a single plane. In the three-dimensional layout of gene chip, this binding reaction occurs through the thickness or depth of the chip. Therefore, depth of field becomes more important since the signal must be collected throughout the thickness of the chip. Conventional commercial microarray readers which use confocal scanning optics are not appropriate for these chips. Only expensive custom-built CCDs are large enough to image the entire microarray in a single detection step. Therefore, confocal concept of acquiring signal from a very thin optical slice, enters in conflict with three dimensional geometry of flow through chip. In order to produce a good lateral resolution to distinguish the individual spot, the light should be collected from the entire thickness of the chip. There is therefore a tradeoff in resolution between lateral and depth of field, and this imposes extra weight to the section criteria. The higher the DNA, the greater lateral and depth resolution is achieved. For example, the image area for 1× objective is:
8.5×6.8 mm
wherein for 40× objective, it is reduced to;
0.22×0.17 mm.

The present invention oblique flow is much different. Indeed, the oblique flow chip has addressed the above problems with a totally new design. As it is shown in FIG. 7 of the drawings, the light or incident ray must penetrate the microchannel top end mouth and excite the fluorescent molecules present inside the sample fluid, and emission light must be able to escape from within the tube. This is achieved at its maximum efficiency when the incident ray is perpendicular to the top free surface of the chip, and reflected ray is zero. In this scenario, all the light will penetrate the tube. By choosing the θ critical angle for maximum internal reflection and minimum loss of refraction to the chip core material, the oblique angle β can be computed. After the fluorescent molecules from within the channel tubes have been excited, most of the emission light will exit perpendicularly to the top chip surface, which will result in an improved optical collection and detection system, as is shown at 20 in FIG. 7.

In oblique flow:
a) there is no need to collect light from within the entire thickness of the tube, since it can be collected from the top microchannel mouth surface 18a surface and act as a flat surface chip. The need for expensive devices with special objective lenses is therefore eliminated.
b) the halo artifact which is seen in conventional three dimensional chip, disappears. This will result in more uniformity and consistency in imaging intensities of various channel when the intensities comparison plays a crucial role in determination of end result. That is to say, as one looks e.g. through an empty tube, the bottom outer end of the tube will obviously disappear from view when the viewer tilts the tube.
c) By increasing the light penetration and emission and maximizing total internal reflection and minimizing the cross-talk, which in turn will increase the detection sensitivity, the channel diameter is allowed to increase, thus enabling decrease of the problem associated with liquid passing through the channels and high pressure vacuum, which jeopardizes the chip structural integrity.

Since the refracted ray is minimized by choosing the right angle θ or critical angle, therefore the cross-talk is minimized.

The cross-talk is an important phenomenon in image analysis. Since most of flat surface chips are scanned using a laser beam, the cross talk could be minimized by directing the incident beam with the appropriate critical angle. This is more noticeable where the light should be travelling through the fiber optics for miles.

On the contrary, in prior art FIG. 6 for example, since the microchannel has non-uniform internal space with different dimension through the length of the chips, the cross-talk reaches its maximum and most light will escape from the channels. Moreover, since the length of the microchannels vary and no two channels are the same, there is various quantity of fluorescein dye bounded to these channels; this will in turn result in various intensity due to uneven quantity of bound molecules.

Figure 8:
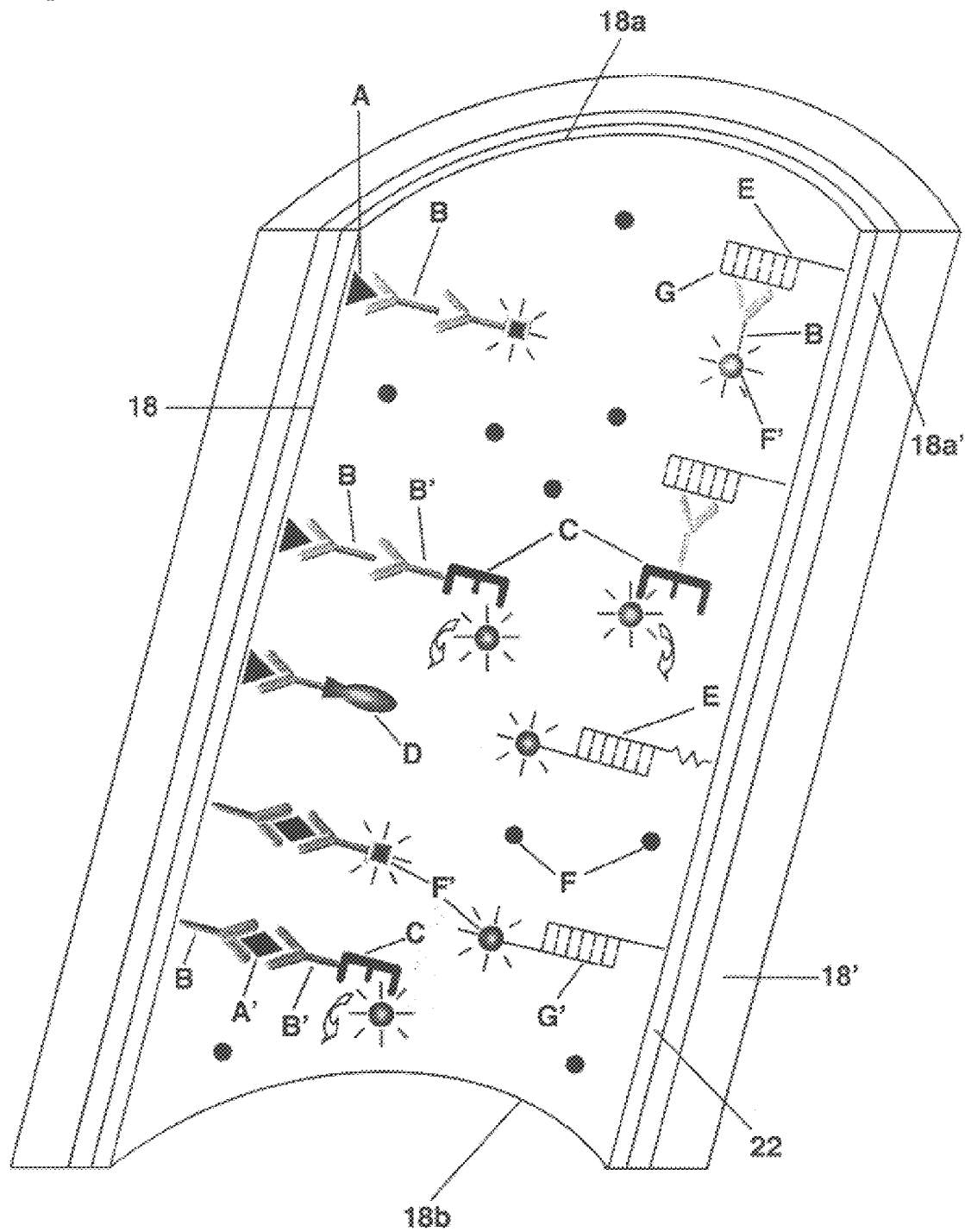
FIG. 8 is a still larger scale sectional view of the slanted channel of FIG. 7, suggesting how the various bio-molecules and proteins adhere to the inside wall of this slanted micro-channel tube of glass plate chip.

FIG. 8 schematically suggests how the biomolecules in the sample solution are bound to the inner wall of the cylindroid channel tube 18. Also in FIG. 8, element 18a' is an interface which has a lower refractive index than element 18. This layer could also be made of reflective metallic coating, such as aluminum or silver for the type of channels with inner metallic coating. These biomolecules may include:

antigens A, connecting antibodies B to the wall of channel tube 18;

enzymes C, conjugated with specific antibodies B' to the antigens A' and antibodies B combination;

gold particles D, also conjugated with specific antibody B;

DNA molecules E, connecting fluorescein molecules in their excited fluorescent state, F', to the inner wall of channel tube 18, or connecting a secondary antibody B being conjugated with a specific enzyme to the inner wall of channel tube 18.

Substrate F is required for colour formation of enzyme C conjugated antibody B'.

It is noted that the issues of critical angle and preferred angle is relevant to the transparent chip embodiment, but not to the chip with reflecting metallic inner coating of the micro-channels. In the latter chip embodiment, once the light enters the micro-channels, it does not have a chance to escape because of metallic coating. The transparent chip is envisioned for use with fluorescent dyes, whereas the metallic coated microchannel chip is envisioned for use mainly for non fluorescent material such as use of particles or gold in detection. The general concept of the metallic coated microchannel chip is that this reflecting inner coating on the inner wall of channels, once a particle or gold tagged biomolecule is used for detection, becomes tarnished so that there appears an opaque or black layer on this reflecting coating surface and light can not pass through efficiently. Therefore, the reduction in light intensity reflection within the channel will determine the property of the biomolecule; it is also a cheaper and easier to implement technique. In the transparent chip concept on the other end, the fluorescent dye produces when excited more light and alerts that there is a positive result. As suggested in FIGS. 10A–31, and 32A–B, 33A–B, it is understood that in the present invention, a single panel chip may consist of millions of primary compartments or unit cells 50, 50', 50", 50'", 50"", 50"'", being arranged in rows and columns in such a fashion that there is a minimum of dead space wasted between cells, while not compromising the structural integrity of the panel chip. Each such unit cell has channels extending through the thickness of the panel chip, which may form non circular layouts such as a slot 100, an arcuate section 102, straight or arcuate segments, 104, 106 respectively, water droplet like slots 108, and various other shapes. These shapes correspond to channels of non cylindroid shape, to accomodate microscopic material of specific size and shape. The length of these slot channels may vary depending on the design and specific physical nature of contaminants, and degree of viscosity of the specific test solution. Each of these unit cells 50, 50', . . . acts as a pixel in imaging. The spot to be placed on the chip should not be smaller than a pixel, but it might cover more than one.

The substrate for fabrication of the chip is preferably selected from the following group of material: polymers and plastics, polypropylene, parylene, polyester, polyimide, polyurethane, polyethylene, polystyrene, glass, silicon dioxide, fused silica, borosilicate, synthetic resins, metal, aluminum, or any other material that is suitable for microfabrication such as silicon wafer and others.

Using the following processes as an example, one can produce the above-noted microchips:

application of laser in micro-machining using mask projection or contact mask, multiple beam system combined with step and repeat sequence;

application of chemical or plasma etching or use of Deep Silicon Ion Etcher (ICP RIE) to create a male device to be used in micro-embossing techniques for creating the desirable patterns on plastics and polymers. ICP RIE allows for incredibly deep highly anisotropic etches of SI, quartz and other materials. This technique covers the most area in panel chip, therefore is more economical.

using various techniques, such as spraying or gas diffusion to cover the panel chip substance of polymers, plastics or metal with a thin layer of silicon dioxide or glass with a thickness of approximately 200 Angstroms (0.02μ), in order to create a desirable surface for binding of DNA and proteins.

The cylindrical pores might optionally be included to further cover between the slots. The porous substrate that is created in this fashion, is capable of binding macromolecules and yet allowing other impurities in test solutions to pass through and be least prone to blockage.

This panel chip may hold a liquid solution, and therefore is suitable for use as a protein chip, where protein requires liquid to hold its 3D configuration for binding. This panel chip might be used for direct synthesis of molecules such as drugs within each pixel, which is used as a separate flask. This technique is used in combinatorial chemistry, where millions of drugs are synthesized simultaneously since each pixel is separated by a wall.

I claim:

1. A rigid panel chip for supporting biological samples for observation with a laser imaging microscope, said panel chip defining a top flat surface, a bottom bearing surface, and a plurality of unit cells extending generally parallel to each other from said top to bottom surfaces, each of said unit cells defining a layout at said top surface of at least two channels arranged in plan view generally symmetrically relative to one another, each of said channels defining a top access mouth for ingress of said biological samples and having such an inner diameter as to accommodate flow through viscosity of a biological sample containing fluid; wherein a sharper and more uniform panel chip channel imaging is achieved.

2. A panel chip as in claim 1, wherein the number of said channels in each of said unit cells can vary between about one and two hundred.

3. A panel chip as in claim 1, wherein the substrate for fabrication of the panel chip is selected from polymers, plastics, polypropylene, parylene, polyester, polyimide, polyurethane, polyethylene, polystyrene, glass, silicon dioxide, fused silica, borosilicate, synthetic resins, metal, and aluminum.

4. A panel chip as in claim 1, wherein said channels layout at said panel top surface in a given unit cell is selected from:
at least three straight slot channels, extending parallel to one another;
an air fan like layout of arcuately shaped "blade" channels, with a central circular "hub" channel forming the top end of a cylindroid channel;
a number of concentrically disposed arcuate channels, with a central circular channel forming the top end of a cylindroid channel; and
a number of cross-shaped disposed straight channels.

5. A panel chip as in claim 1, wherein said channels layout at said panel top surface in a given unit cell includes a number of star shaped disposed straight channels.

6. A panel chip as in claim 5, further including a pair of straight channels, much shorter than said star shaped disposed channels and disposed parallel to one another within a free area centrally of said star shaped disposed channels.

7. A panel chip as in claim 5, further including a plurality of circular channels, disposed concentrically of said star shaped disposed channels.

8. A panel chip as in claim 5, further including a plurality of additional shorter straight segments channels, each disposed concentrically of said star shaped disposed channels in between a pair of successive said star shaped disposed channels but at a distance from the center of the unit cell.

9. A panel chip as in claim 1, wherein said channels layout at said panel top surface in a given unit cell includes a number of C-shaped channels successively disposed circumferentially thereof in the same general trough-facing circular direction.

10. A panel chip as in claim 9, further including a number of circular channels, disposed within said C-shaped channels.

11. A panel chip as in claim 9, further including a plurality of shorter straight segments channels, disposed within said C-shaped channels.

12. A panel chip as in claim 1, wherein said channels layout at said panel top surface in a given unit cell includes a pair of triplets of C-shaped channels disposed in facing opposing register relative to one another.

13. A panel chip as in claim 12, further including a plurality of circular channels, sparsely settled about said C-shape channels.

14. A panel chip as in claim 12, further including a plurality of shorter straight channels, sparsely settled in between each pair of successive C-shape channels.

15. A panel chip as in claim 1,
wherein said channels layout at said panel top surface in a given unit cell includes a plurality of radially extending waterdroplet like channels.

16. A panel chip as in claim 1,
wherein said channels layout at said panel top surface in a given unit cell includes a few waterdroplet like channels, disposed parallel to one another.

17. A panel chip as in claim 2,
wherein the number of said channels range between 2 and 50.

18. A rigid panel chip for supporting biological samples for observation with a microscope, said panel defining a top flat surface, a bottom bearing surface, and a plurality of unit cells extending generally parallel to each other from said top to bottom surfaces, each of said unit cells defining at least one non cylindroid slot channel, said slot channel defining a top access mouth for ingress of said biological samples and having such an inner diameter as to accommodate flow through viscosity of a biological sample containing fluid; said slot channel having a shape selected from a straight slot, an arcuate slot and a water droplet like slot;

wherein a sharper and more uniform panel chip channel imaging is achieved.

* * * * *